(12) United States Patent
Sunshine et al.

(10) Patent No.: US 6,450,008 B1
(45) Date of Patent: Sep. 17, 2002

(54) FOOD APPLICATIONS OF ARTIFICIAL OLFACTOMETRY

(75) Inventors: Steven A. Sunshine; Ajoy Roy, both of Pasadena; Jing Li, Temple City, all of CA (US)

(73) Assignee: Cyrano Sciences, Inc., Pasadena, CA (US)

( * ) Notice: Subject to any disclaimer, the term of this patent is extended or adjusted under 35 U.S.C. 154(b) by 0 days.

(21) Appl. No.: 09/619,819

(22) Filed: Jul. 20, 2000

Related U.S. Application Data

(60) Provisional application No. 60/145,352, filed on Jul. 23, 1999.

(51) Int. Cl.[7] ............................................. G01N 33/497
(52) U.S. Cl. ..................... 073/23.34; 73/23.2; 702/27
(58) Field of Search .............................. 73/23.34, 23.2; 205/737; 702/27, 32

(56) References Cited

U.S. PATENT DOCUMENTS

| | | | |
|---|---|---|---|
| 4,314,027 A | 2/1982 | Stahr | |
| 5,675,070 A | 10/1997 | Gelperin | |
| 5,788,833 A | 8/1998 | Lewis et al. | 205/787 |
| 6,085,576 A * | 7/2000 | Sunshine et al. | 73/29.01 |
| 6,170,318 B1 * | 1/2001 | Lewis | 73/23.34 |
| 6,244,096 B1 * | 6/2001 | Lewis et al. | 73/23.2 |

FOREIGN PATENT DOCUMENTS

| | | |
|---|---|---|
| WO | WO 99/27357 A | 6/1999 |
| WO | WO 99/66304 A | 12/1999 |
| WO | WO 00/26638 A | 5/2000 |

OTHER PUBLICATIONS

Cowell et al., "Sensors for Citrus Fruit Quality," *Life Chemistry Reports*, 1994, vol. 11, pp. 333–338.

Stetter et al., "Quality classification of grain using a sensor array and pattern recognition," *Analytica Chimica Acta*. 284, Elsevier Science Publisher B.V., Amsterdam (1993), pp. 1–11.

Winquist et al., "Performance of an electronic nose for quality estimation of ground meat," *Measure. Sci. Technol.* (1993), pp. 1493–1500.

* cited by examiner

*Primary Examiner*—Hezron Williams
*Assistant Examiner*—Charles D Garber
(74) *Attorney, Agent, or Firm*—Townsend and Townsend and Crew, LLP (57) ABSTRACT

The present invention relates generally to methods and devices for evaluating agriculture products, and more particularly, to assessing and monitoring the quality of food products using electronic noses. A quality control monitoring device (10) is provided having first sensor array (13) located in a first vessel (11) and a second sensor array (14) located in a second vessel (12). An analyzer (15) is set-up with a display (16).

14 Claims, 5 Drawing Sheets

FOOD APPLICATIONS OF ARTIFICIAL OLFACTOMETRY

CROSS REFERENCE TO RELATED APPLICATIONS

The present application claims priority to U.S. Provisional Patent Application No. 60/145,352, filed Jul. 23, 1999, and incorporated herein by reference in its entirety for all purposes.

FIELD OF THE INVENTION

The present invention relates generally to methods and devices for evaluating agriculture products, and more particularly, to assessing and monitoring the quality of agricultural products, such as food products, using electronic noses.

BACKGROUND OF THE INVENTION

In general, electronic noses comprise an array of chemical sensing elements and a pattern recognition system. Electronic noses are designed to analyze complex vapors as they exist and produce a unique signature output. The sensor array is designed to respond to many different individual and complex compounds, analytes and vapors.

One recognized area of commercial interest for electronic noses is the food industry. Applications include quality assessment in food production, inspection of food quality by odor, control of food cooking processes, inspection of fish and monitoring of fermentation processes. Flavor is generally the most important sensory characteristic associated with foods. Flavor perception consists of two components i.e., taste and aroma. Taste arises from the perception of nonvolatile compounds whereas aroma is a result of the many hundreds of volatile compounds associated with food.

Researchers have investigated the response of an array of twelve tin oxide sensors to headspace of coffee packs. In that study, discriminate and classification function analyses were performed on the sensor array response to three commercial coffees as well as one coffee subjected to a range of six roasting times. The feasibility of using an electronic nose to classify coffee aromas was demonstrated with greater than 80% accuracy (see, Gardner et al., Sensor and Actuators B, 6, 71–75 (1992)).

In addition, a multisensor system was developed to discriminate between the aromas of different beers. In that study, 24 conducting polymer sensors were constructed to respond differently to the headspaces of beers and lagers. The output from the polymer array was preprocessed using a variety of algorithms and then classified using statistics (see, Gardner et al., Sensor and Actuators B, 18–19, 240–243 (1994)).

Moreover, U.S. Pat. No. 5,675,070, which issued to Gelperin, discloses an artificial olfactory system and associated method for identifying an object by its aroma. The artificial olfactory system includes a testing chamber in which are disposed an array of gas sensors. The object to be identified is placed in close proximity to the testing chamber. The air pressure within the testing chamber is then lowered below ambient, thereby causing ambient air to flow past the object being identified and into the testing chamber. As air flows past the object being identified, the aroma of the object becomes mixed with the air and is carried into the testing chamber. Once within the testing chamber, the air/aroma mixture is exposed to the array of gas sensors. The gas sensors detect the levels of various gases comprising the air/aroma mixture and produce a sensor pattern that represents the various gas concentrations detected.

Despite the advances made in the prior art, none of the aforementioned systems are designed for process monitoring "on-line" or "on-the-fly." The prior art methods are performed "off-line" which is inefficient and takes more time. Thus, there exists a need for an electronic nose that is suitable for applications in food that allows for on-line analyses. The present invention fulfills these and other needs.

SUMMARY OF THE INVENTION

In certain aspects, the present invention provides "in-line" or "on-line" monitoring of agricultural product qualities and agricultural product processes. As such, the present invention provides a method for monitoring a quality of an agricultural product on-line, comprising: training an array of sensors with a fluid associated with a known agricultural product to generate an acceptance level; contacting the array of sensors with the fluid or vapor associated with an unknown agricultural product to generate a response level; and comparing the response level with the acceptance level thereby monitoring the quality of the agricultural product on-line. As used herein, the term "fluid" refers to a solid, a liquid, a gas or a vapor.

In certain aspects, the agricultural product or process is exposed to a first sensor array to generate a first response. After the process is complete, or after a reactant is added, the product is contacted with a second sensor array to generate a second response. Preferably, the first sensor array and the second sensor array use similar, or the same sensing elements in each of the arrays. In this aspect, a comparison is made between a sample before it undergoes a process, such as a blending process, and then after the blending process is complete. By subtracting the second response from the first response, a difference pattern is obtained and thus, it is possible to ascertain the completeness of the process. Suitable processes include, but are not limited to, formulating, blending, mixing, reacting, pilot plant processing, determining the presence of microorganisms, etc.

In another embodiment, the present invention provides a method for differentiating between a quality of an agricultural product comprising: contacting a fluid associated with a first agricultural product with a sensor array to generate a first response; ii) contacting a fluid associated with a second agricultural product with the sensor array to generate a second response; and iii) comparing the first response with the second response, thereby differentiating between a quality of the agricultural product. In certain preferred aspects, the method is used to differentiate between product from various geographical origins, such as grapes from various regions.

In certain other embodiments, the present invention provides a quality control monitoring device, wherein the device comprises: i) a first sensor array at a first location to generate a first response; ii) a second sensor array at a second location to generate a second response; and iii) an analyzer to compare the first response with the second response.

In still yet another embodiment, the present invention provides a method for monitoring a quality of an agricultural product, comprising: (i) training an array of sensors with a fluid associated with a known agricultural product to generate a first residual standard deviation $(s(e)^2)$; (ii) contacting the array of sensors with the fluid associated with an unknown agricultural product to generate a second residual standard deviation $(s(e_m)^2)$; (iii) calculating a ratio between the second residual standard deviation and the first residual standard deviation $(s(e_m)^2/s(e)^2)$; and (iv) comparing the ratio with an acceptability quotient $(F_{1,df,\alpha})$ thereby monitoring the quality of the agricultural product. In certain preferred embodiments, the acceptability quotient is user selected. This selection can then be changed during the duration of an in-line process.

Using the devices and methods of the present invention, it possible to monitor various processes, such as agricultural processes, including for example, product formulating, product blending, determining the presence of pathogenic microorganisms, and the like.

Various qualities of agricultural products are suitably monitored using the methods and devices of the present invention. These qualities include, but are not limited to, fruit ripening, product blending, product formulation, product mixing, determining rancidity, determining authenticity and cooking processing.

These and other aspects of the present invention will become more readily apparent when read with the accompanying figures and detailed description which follow.

DETAILED DESCRIPTION OF THE INVENTION AND PREFERRED EMBODIMENTS

In certain embodiments, the present invention relates to methods for monitoring a quality of an agricultural product "on-line." As used herein, "on-line" refers to a method of monitoring a process, such as a chemical process. In certain aspects, by using the methods and devices of the present invention, it is not necessary to remove a test sample from a reaction to perform the monitoring of the product quality. Preferably, using the present methods and devices, analytical determinations such as quality control, can be performed in situ.

As such, in one embodiment, the present invention provides a method for agricultural product quality monitoring on-line comprising: training an array of sensors with a fluid or vapor associated with a known agricultural product to generate an acceptance level; contacting the array of sensors with the fluid or vapor associated with an unknown agricultural product to generate a response level; and comparing the acceptance level with the response level thereby monitoring the agricultural product quality on-line. As used herein, the term monitoring refers to measuring, identifying, detecting, analyzing or combinations thereof.

The training of the system is done using an artificial neural network. Using a representative number of test samples for each quality to be monitored, it is possible to generate an acceptance level. In general, artificial neural networks (ANN) are used to analyze complex data and to recognize patterns. Neural networks are dynamic systems that have interacting parts called neurons, nodes or computational units, which can change their connections to learn from incoming data. Flexible connections allow a neural network to evolve and adapt to changing sensory input data. Neural networks are given examples of data as input such as responses to a desired quality, and they produce an output. They are trained by being corrected, on the basis of comparisons to a predefined, standard output of the desired quality e.g. whether the fruit is ripe or whether the grape is from Napa Valley (authenticity), etc.

A neural network has an input layer, processing layers and an output layer. The information in a neural network is distributed throughout the processing layers. The processing layers are made up of nodes that simulate the neurons by its interconnection to their nodes.

In operation, when a ANN is combined with a sensor array, the sensor data is propagated through the networks. In this way, a series of vector matrix multiplications are performed and unknown agricultural product qualities can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In a preferred embodiment, the Fisher linear discriminant analysis (FLDA) and canonical discriminant analysis (CDA) and combinations thereof are used to assess patterns in responses from the electronic nose.

After the ANN is trained, it is then possible to set an acceptance level. For instance, the methods and devices of the present invention can be designed to improve food and drink qualities, amounts of carbonation in drinks, monitor formulations, monitor quality of bulk materials, and determining whether materials contain microorganisms, e.g., *E. coli* 0157:H7.

The array of sensors is contacted with the fluid or vapor associated with an unknown agricultural product quality to generate a response level. To generate the response level the unknown sample data is passed through the ANN to produce an output (response level). The response level is compared with the acceptance level thereby monitoring the agricultural product for example on-line. This acceptance level can be a pass/fail limit i.e., the presence of *E. coli* 0157:H7 or the absence of *E. coli* 0157:H7.

In certain instances, the array of sensors is in a handheld device. A suitable handheld device is described in U.S. Pat. No. 6,085,676, issued to Sunshine et al., on Jul. 11, 2000, and incorporated herein by reference in its entirety for all purposes.

In another embodiment, measurements using electronic noses of the present invention provide a two-dimensional data set. In this aspect, the rows represent samples and the columns represent responses i.e., variables generated from each sensor. For example, if the number of sensors is 32, there are 32 variables generated for each measurement. The two-dimensional data set is usually called the X-matrix. The individual variables are called the x- or independent variables.

In certain instances, a smaller data set is generated with fewer variables that contains all the useful information from the 32 variables data set (i.e., the X-matrix). In this smaller data set, the redundancy and smaller noise variabilities are removed. One technique used for such data compression and information extraction is principal component analysis. The purpose of PCA is to express the main information in the X-matrix wherein $X=\{X_k, k=1,2, \ldots, K\}$ by a smaller number of variables $T=\{t_l \ldots, t_A\}$ wherein A<K, and wherein T are the principal components of X.

In certain aspects, it is desirable to monitor a quality of an agricultural product wherein a user trains a system with a set of samples with a known quality i.e., the quality is known to be acceptable (e.g., the fruit is ripe). This is known as the calibration data set. Next, the user selects an acceptability quotient that determines how far from this acceptable population an unknown agricultural product or quality can be, and still be classified as acceptable. Finally, the user measures an unknown sample and, in conjunction with the acceptability quotient, the system determines whether or not the sample is acceptable.

Using principal component analysis as set forth above, the calculation of principal components, quotients and the corresponding confidence (acceptability) limits involve the following steps:

For a given data set (X matrix with M rows (M samples) and K columns), the covariance matrix of X is defined as:

$$cov(X)=X^TX/(M-1) \text{ wherein T means transpose.} \quad \text{I}$$

The columns of X are assumed to be mean-centered. If the columns are autoscaled, it is possible to obtain a correlation matrix instead of a covariance matrix. In most instances, data are usually mean-centered or auto-scaled. X is then expressed as:

$$X=t_1p_1^T+t_2p_2^T+\ldots+t_Ap_A^T+E \quad \text{II}$$

In Formula III below, the $p_i$'s are eigenvectors of the covariance (or correlation) matrix cov(X).

$$cov(X)p_i=\lambda_i p_i \quad \text{III}$$

The $t_i$'s can be calculated as set forth in formula IV:

$$t_i=Xp_i \quad \text{IV}$$

Usually, data can be expressed by fewer 't' variables (factors) than original variables. The variables "$\lambda_i$" measure the amount of variance captured by the variables "$t_i$". Moreover, $t_1$ captures the greatest amount of variance in the data set, followed by $t_2$, $t_3$, etc.

From the error (residual) term E in formula II, the total residual standard deviation for a given set of acceptable samples (i.e., the calibration data set) is calculated as follows:

$$s(e)^2 = \sum_{m=1}^{M}\sum_{k=1}^{K} e_{mk}^2/df, \quad \text{V}$$

wherein, in formula V, df is the degrees of freedom. The degrees of freedom is equal to M-1 wherein M is the number of samples. Those of skill in the art will realize there are other ways to define degrees of freedom.

Thus, for an unknown sample "i", similar to the known samples, the standard residual deviation is calculated as follows:

$$s(e_m)^2 \sum_{k=1}^{K} e_{mk}^2 \quad \text{VI}$$

Therefore, the ratio "$s(e_m)^2/s(e)^2$" can be determined. The ratio is then compared with the acceptability quotient, "$F_{1,df,\alpha}$" which is a F-statistics value at 1 degree of freedom for the numerator, df, the degrees of freedom for the denominator, and a predetermined $\alpha$ (e.g., 0.05). If the ratio is greater than the acceptability quotient, the sample is tagged as unacceptable at 95% confidence limit ($\alpha$ is 0.05). Alternatively, if the ratio "$s(e_m)^2/s(e)^2$" is greater than a constant (e.g., 5 or 7), the sample can be tagged as unacceptable. Those of skill in the art will know of other variations of residual statistics calculations.

As such, in another embodiment, the present invention provides a method for monitoring a quality of an agricultural product, comprising:

(i) training an array of sensors with a fluid associated with a known agricultural product to generate a first residual standard deviation $(s(e)^2)$;

(ii) contacting the array of sensors with the fluid associated with an unknown agricultural product to generate a second residual standard deviation $(s(e_m)^2)$;

(iii) calculating a ratio between the second residual standard deviation and the first residual standard deviation $(s(e_m)^2/s(e)^2)$; and (iv) comparing the ratio with an acceptability quotient $(F_{1,df,\alpha})$ thereby monitoring the quality of the agricultural product.

In certain other instances, the Hotelling variable "$T^2$" is used for acceptability of an unknown sample. The Hotelling $T^2$ for the unknown is calculated as set forth below:

$$T_i^2=t_i\lambda^{-1}t_i. \quad \text{VII}$$

The average $T^2$ for the calibration set is "$A(M-1)/(M-A)$". Again, the ratio, $T_i^2/(A(M-1)/(M-A))$ for an unknown sample is calculated and compared with the acceptability quotient which is the $F_{A,M-A,\alpha}$ statistics value. If the ratio is greater than the acceptability quotient, the unknown sample is tagged as unacceptable.

In certain preferred embodiments, the acceptability quotient is user selected. This selection can then be changed during the duration of an in-line process. Depending on the particular circumstances, the acceptability quotient can be tightened or loosened by the program operator as the agricultural product quality is monitored.

In another aspect, the Mahalonobis distance is calculated instead of the Hotelling $T^2$. Moreover, in other instances, any individual t (e.g., $t_1$) is used as a control variable. If the $t_1$ for an unknown sample is outside $\pm 5\sigma$ ($\sigma$=standard deviation) of the average $t_1$ for a calibration set, the sample is tagged as unacceptable. The limit can be other than $\pm 5\sigma$ (e.g., $\pm 7\sigma$).

Suitable processes and qualities which can be monitored using the devices and methods of the present invention include, but are not limited to, quality control processes, extraction processes, process development processes, process research processes, mixing processes and detection and identification of microorganisms such as pathogenic bacteria detection, etc.

In yet another embodiment, the present invention provides a method for differentiating between a quality of an agricultural product comprising: contacting a fluid associated with a first agricultural product with a sensor array to generate a first response; ii) contacting a fluid associated with a second agricultural product with the sensor array to generate a second response; and iii) comparing the first response with the second response, thereby differentiating between a quality of an agricultural product.

Suitable agricultural product qualities include, but are not limited to, rancidity of meat, grain, milk, oil, off-odor due to degradation, stabilization of products, such stabilized rice-bran, authenticity of products, such as geographic region determination of grapes, coffee, etc. and the origin of products.

In certain preferred aspects, the present invention provides a quality control monitoring device, wherein the device comprises: i) a first sensor array at a first location to generate a first response; ii) a second sensor array at a second location to generate a second response; and iii) an analyzer to compare the first response with the second response.

Figure 1:
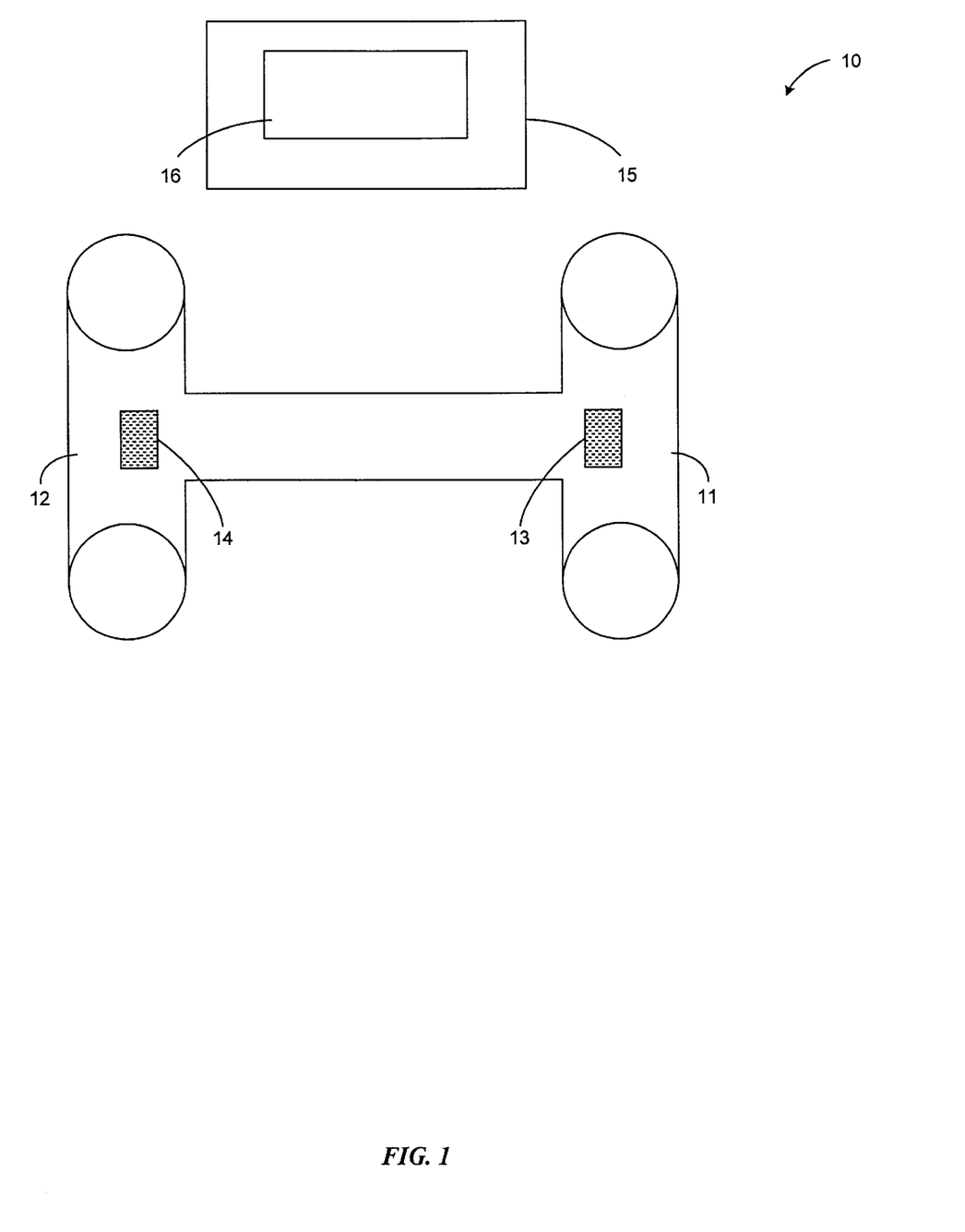
FIG. 1 shows a side-view of a reaction-monitoring device of the present invention.

With reference to FIG. 1, one embodiment of a quality control monitoring device (10) is shown. In this embodiment, a first sensor array (13) is located in a first vessel (11) and a second sensor array (14) is located in a second vessel (12). An analyzer (15) is set-up with a display (16).

As such, the present invention provides a method for monitoring a quality of a reaction comprising: i) contacting a fluid associated with the reaction with a first sensor array to generate a first response; ii) contacting a fluid associated with the reaction with a second sensor array to generate a second response; and iii) comparing the first response with the second response, thereby monitoring the quality of the reaction.

In certain embodiments, the analyzer is configured to analyze a particular response from the sensors and to identify, quantify, or compare responses. For example, in certain embodiments, each sensor has a resistance that varies according to a concentration of one or more analytes. Conditioning circuitry is coupled to the chemically sensitive sensors and generates an analog signal indicative of the resistance of the sensors. An analog-to-digital-converter (ADC) is coupled to the conditioning circuitry and provides a digital signal in response to the analog signal. The analyzer couples to the ADC and determines, based on the digital signal, the identity or concentration of the analyte(s) or can compare various responses. As used herein, the analyzer can be a processor, a DSP processor, a specially designed ASIC, or other circuits designed to performed the analysis functions described. The analyzer can also be a general-purpose processor executing program codes written to perform the required analysis functions.

Sensor Arrays

The devices and methods of the present invention include an array of sensors and, in certain instances, the sensors as described in U.S. Pat. No. 5,571,401 are used. Sensors suitable for detection of analytes associated with agricultural products include, but are not limited to, surface acoustic wave (SAW) sensors; quartz microbalance sensors and Taguchi gas sensors; conductive composites resitors; metal oxide gas sensors, such as tin oxide gas sensors; organic gas sensors; metal oxide field effect transistor (MOSFET); piezoelectric devices; infrared sensors; sintered metal oxide sensors; metal gate MOSFET, such as Pd-gate MOSFET; phthalocyanine sensors; electrochemical cells; conducting polymer sensors; catalytic gas sensors; organic semiconducting gas sensors; solid electrolyte gas sensors; temperature sensors, humidity sensors, piezoelectric quartz crystal sensors; and Langmuir-Blodgett film sensors.

In a preferred embodiment, the sensors of the present invention are disclosed in U.S. Pat. No. 5,571,401, incorporated herein by reference. Briefly, the sensors described therein are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors and in certain instances 1000 or more sensors. The array of sensors can be formed on an integrated circuit using semiconductor technology methods, an example of which is disclosed in PCT patent application Ser. No. WO 99/08105, entitled "*Techniques and Systems for Analyte Detection*," published Feb. 19, 1999, and incorporated herein by reference. Another preferred sensor is disclosed in WO 99/27357 entitled "*Materials, Method and Apparatus for Detection and Monitoring Chemical Species*," published Jun. 3, 1999.

Preferably, the sensor arrays of the present invention comprise at least one sensor selected from the following group of sensors, inorganic metal oxide semiconductors such as tin-oxide based sensors, organic conducting polymers such as polymers of pyrrole and aniline, mass sensitive piezoelectric sensors such as bulk acoustic wave and surface acoustic wave sensors and nonconducting/conducting regions sensors.

As will be apparent to those of skill in the art, the sensors making up the array of the present invention can be made up of various sensor types as set forth above. For instance, the sensor array can comprise a conducting/nonconducting regions sensor, a SAW sensor, a metal oxide gas sensor, a conducting polymer sensor, a Langmuir-Blodgett film sensor, and combinations thereof.

In certain embodiments, the temporal response of each sensor (response as a function of time) is recorded and can be displayed. Various responses include, but are not limited to, frequency, temperature, potential, current, resistance, impedance, capacitance, inductance, magnetic, optical, etc. The temporal response of each sensor can be normalized to a maximum percent increase and percent decrease that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, a measuring device for detecting responses across each sensor, a computer, a display, a data structure of sensor array response profiles, and a pattern recognition algorithm(s) or comparison tables are provided. In another embodiment, the electrical measuring device or detector is an integrated circuit comprising neural network-based hardware and a digital-analog converter (DAC) multiplexed to each sensor, or a plurality of DACs, each connected to different sensor(s).

Agricultural Products and Qualities

A wide range of agricultural products can be used in the methods and devices of the present invention. Suitable agricultural products include, but are not limited to, fruit, oil, grapes, vegetables, grains, corn, rice, soybean, cotton, coffee, wine, meat, beef, pork, lamb, fish, diary products, soft drinks, food products, carbonated soda, dry bulk materials, liquid, solids, etc.

Suitable agricultural product qualities include, but are not limited to, rancidity of meat, milk, oil, off-odor due to degradation, stabilization of products, such stabilized rice-bran, authenticity of products, such as geographic region determination of grapes, coffee, etc., origin of products, quality control, efficiency of extraction, process development qualities, process research qualities, pilot plant operations, fruit ripening, flow rate determination qualities, detection and identification of microorganisms, such as bacteria detection e.g., *E. coli* 0157:H7, detection of viruses, detection of fungi, process improvement qualities, quality of raw materials, headspace sampling, cooking, etc.

Although there are many strains of *E. coli* commonly found in the environment and some with beneficial uses, the strain 0157:H7 is extremely virulent. *E. coli* 0157:H7 is found in the intestinal tract and feces of both animals and man, and can be transmitted by numerous routes: from animal to animal, animal to person, animal to person on food, and person to person through close contact. Although it can survive both refrigeration and freezing, the pathogen is destroyed by thorough cooking.

According to the Centers for Disease Control and Prevention, as many as 20,000 cases of *E. coli* 0157:H7 infection may occur annually. Symptoms of *E. coli* food poisoning include severe abdominal cramps, followed by watery diarrhea that often becomes bloody. Individuals also may experience vomiting and nausea, accompanied by low-grade fever. In children, the elderly and immune-compromised individuals, the infection can lead to kidney failure and possible death.

Undercooked ground beef represents one of the greatest risks of *E. coli* due to its handling and preparation, but outbreaks also have been traced to undercooked roast beef, raw milk, improperly processed cider, contaminated water and mayonnaise, and vegetables grown in cow manure. Using the methods and devices of the present invention, it is possible to detect and identify microorganisms, such as *E. coli* 0157:H7, salmonella, commonly found in poultry; Staphylococcus aurus, a common type of food poisoning; and Listeria monocytogenes, which can result in severe blood poisoning and meningitis.

In certain embodiments, the agricultural products are genetically engineered; such as genetically engineered to withstand herbicides. These genetically engineered crops include, but are not limited to, corn, soybean such as ROUND-UP READY® soybeans, tomatoes, cotton and potatoes. In general, in genetically engineered crops, bacteria, viruses and genes from tobacco or petunia plants are inserted into soy, corn, cotton and canola plants so plants can survive field applications of weed killers. In other instances, a gene form *Bacillus thuringiensis* (Bt), a bacterium found in soil, is inserted into corn, cotton and potatoes to produce a protein toxic to pests that feed on them. The methods and devices of the present invention are especially useful for genetically engineered agricultural products.

Moreover the methods and devices of the present invention can be used for residue analysis of certain herbicides and pesticides. In this aspect, the methods and devices of the present invention can be used for analysis for fungicides, analysis for pesticides, analysis for herbicides, analysis for long-term residues of chlorinated hydrocarbons like DDT and PCB's, analytical support for pesticide fate studies and analytical support for new use studies.

EXAMPLES

The following examples are offered to illustrate, but not to limit, the claimed invention.

Example 1

This Example illustrates the discrimination and identification of cooked rice using methods of the present invention.

A 32 polymer-carbon black sensor array was used to test the headspace samples from three types of cooked rice that have different odors. Fisher linear discriminant analysis (FLDA) and canonical discriminant analysis (CDA) were two of the techniques applied to analyze the data. These algorithms provide the correct cross-validated prediction rate to be 90% or greater.

This study confirmed that a polymer-carbon black sensor array could discriminate among three kinds of rice having different strengths and types of odors. In this study, three types of rice were cooked and sealed in thirty 10 mL bottles with the same amount, ten bottles for each kind of rice.

The sensor responses were collected using a 32 polymer carbon-black sensor array. The raw data were reduced in Excel by taking the maximum data point and averaging three minimum data points to get the $\Delta R/R_o$. The data set of responses was further analyzed using different algorithms, principal component analysis (PCA), soft independent modeling of class analogy (SIMCA), K-nearest neighbors (KNN), FLDA and CDA.

The three kinds of rice were designated as follows:

Medium grain rice labeled 'a',

Medium grain rice labeled 'c',

Medium grain rice labeled 'l'. A human panel scored them and rice labeled "i" was acceptable.

EXPERIMENTAL

Sample preparation:

Raw rice was weighed to 5 g and placed in 10 mL bottles, which took half of the volume of the bottle. Rice cooking: boiled 2 cups of water (arrowhead) in a 2 quart pot, then added 1 cup of rice and reduced the heat to simmer for 20 min. Cooked rice was weighed to 3.85 g and placed in 10 mL bottles, which took half of the volume of the bottle.

Testing conditions

The temperature setting for the headspace sampler was 45° C. in the oven, 50° C. for the loop, 60° C. for the transfer line and 70° C. at the output to the electronic nose. Event times: headspace cycle time was 5 min., vial equilibrium time was 20 min., pressurization time was 0.3 min., loop fill time was 0.15 min., loop equilibrium time was 0.02 min., injection time was 0.3 min. The carrier gas was helium, and the sensor substrates were maintained at 28° C.

RESULTS AND DISCUSSION

Figure 2:
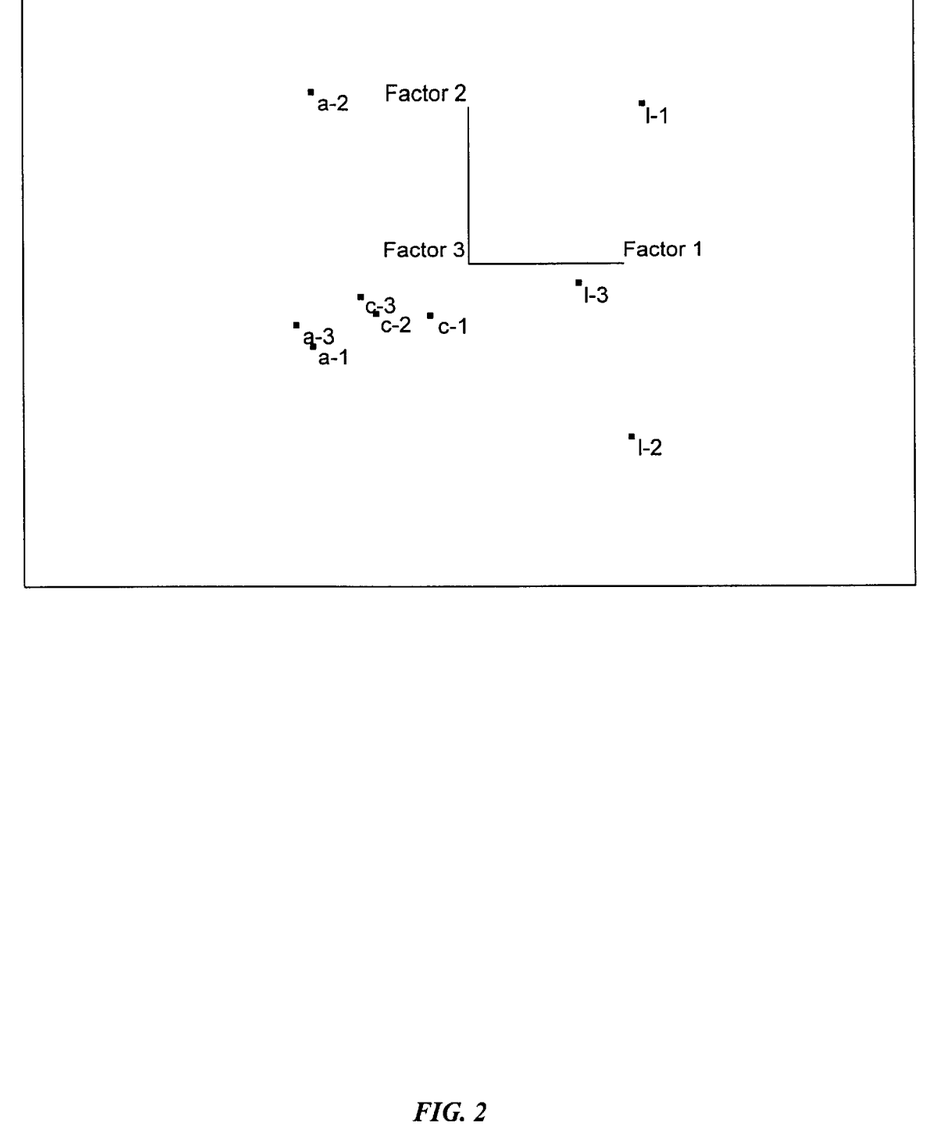
FIG. 2 illustrates monitoring of raw rice samples using methods of the present invention.
Figure 3:
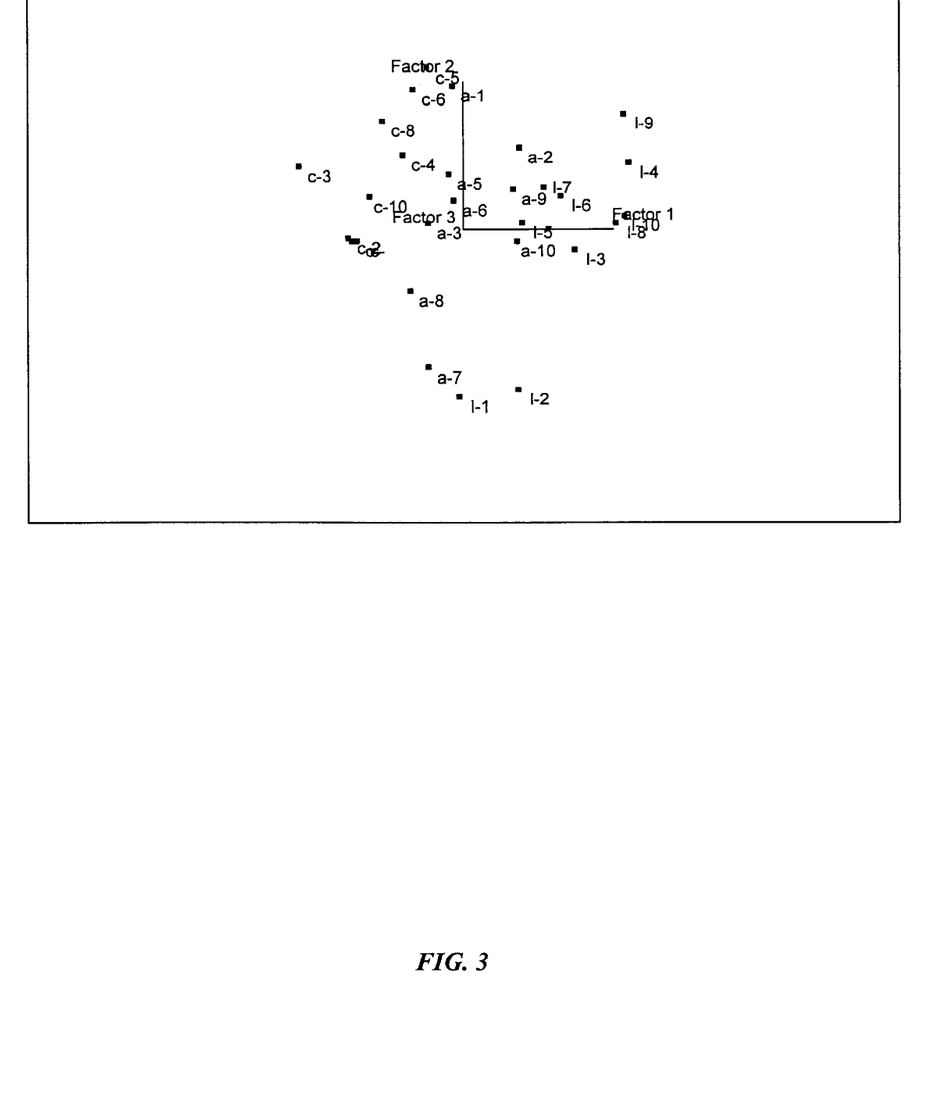
FIG. 3 illustrates monitoring of cooked rice samples using methods of the present invention.

The data were collected with an electronic nose and reduced in Excel by taking the maximum data point and averaging three minimum data points to get the $\Delta A/R_o$. The reduced data were then analyzed using principal component analysis (PCA). The PCA plot (see, FIG. 2) of raw rice shows good separation among these three types of rice. The PCA plot (see, FIG. 3) of cooked rice shows some degree of separation among these three kinds of rice with one 'a' type data point and one 'l' type data point mixed together.

The cooked rice data were further analyzed using KNN, SIMCA, FLDA and CDA. In the case of FLDA and CDA, principal component scores were calculated globally over the primary data set and used as input to the respective analyses (FLDA and CDA). The cross-validated prediction results from these analyses were as follows: KNN gave the correct prediction rate 82%; SIMCA gave the correct prediction rate 82%; FLDA (fisher linear discrimination analysis) gave the correct prediction rate 89%; and CDA gave the correct prediction rate 96%. The conclusion is that the electronic nose of the present invention can identify cooked rice with high precision.

Example 2

This Example illustrates the determination of an acceptability quotient.

Figure 4:
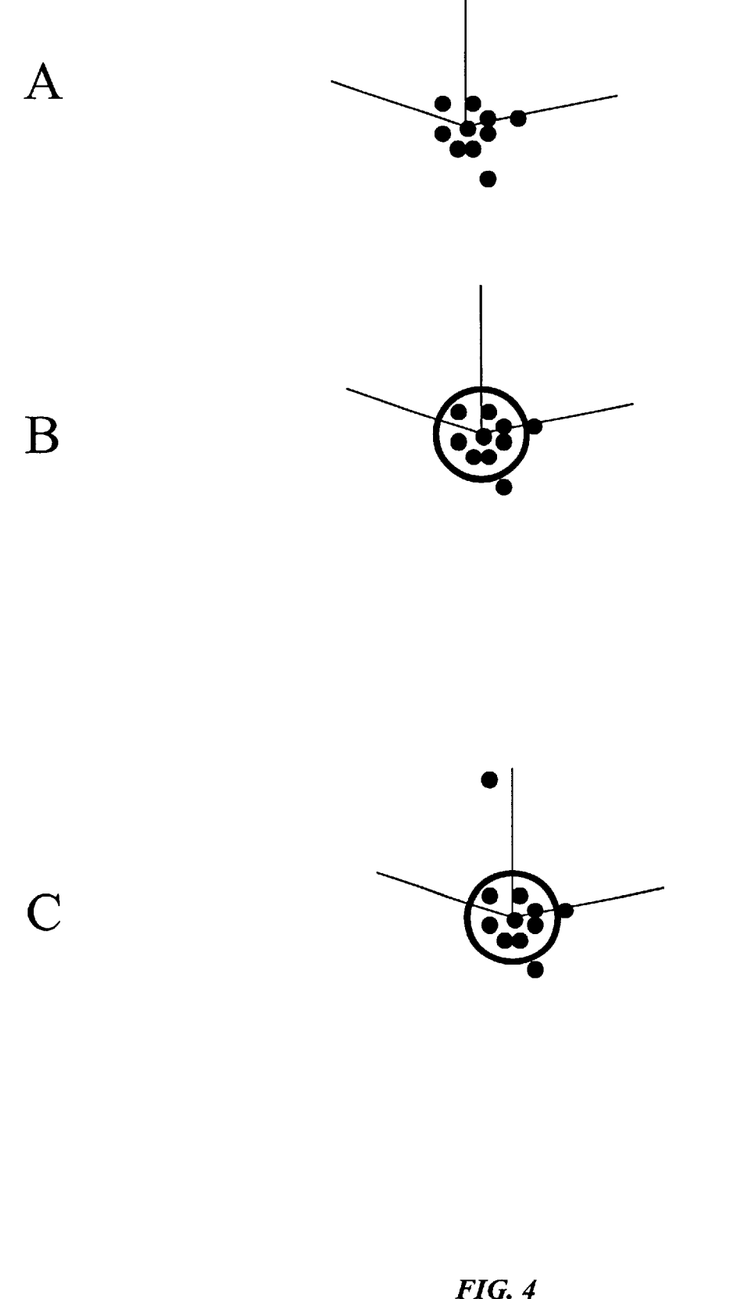
FIG. 4 (A–C) illustrates a process of the present invention. Panel A illustrates a calibration data set. Panel B illustrates an acceptability quotient as depicted by a circle. Panel C illustrates an unacceptable data point.

As illustrated in FIG. 4, a data set of acceptable samples having acceptable qualities is measured. One then effectively trains the electronic nose with the acceptable qualities. This is known as the calibration set. Next, the user selects an acceptability quotient as depicted by the circle surrounding the data. After an unknown is measured, it is compared to the acceptability quotient. The system then decides whether the sample is unacceptable.

Figure 5:
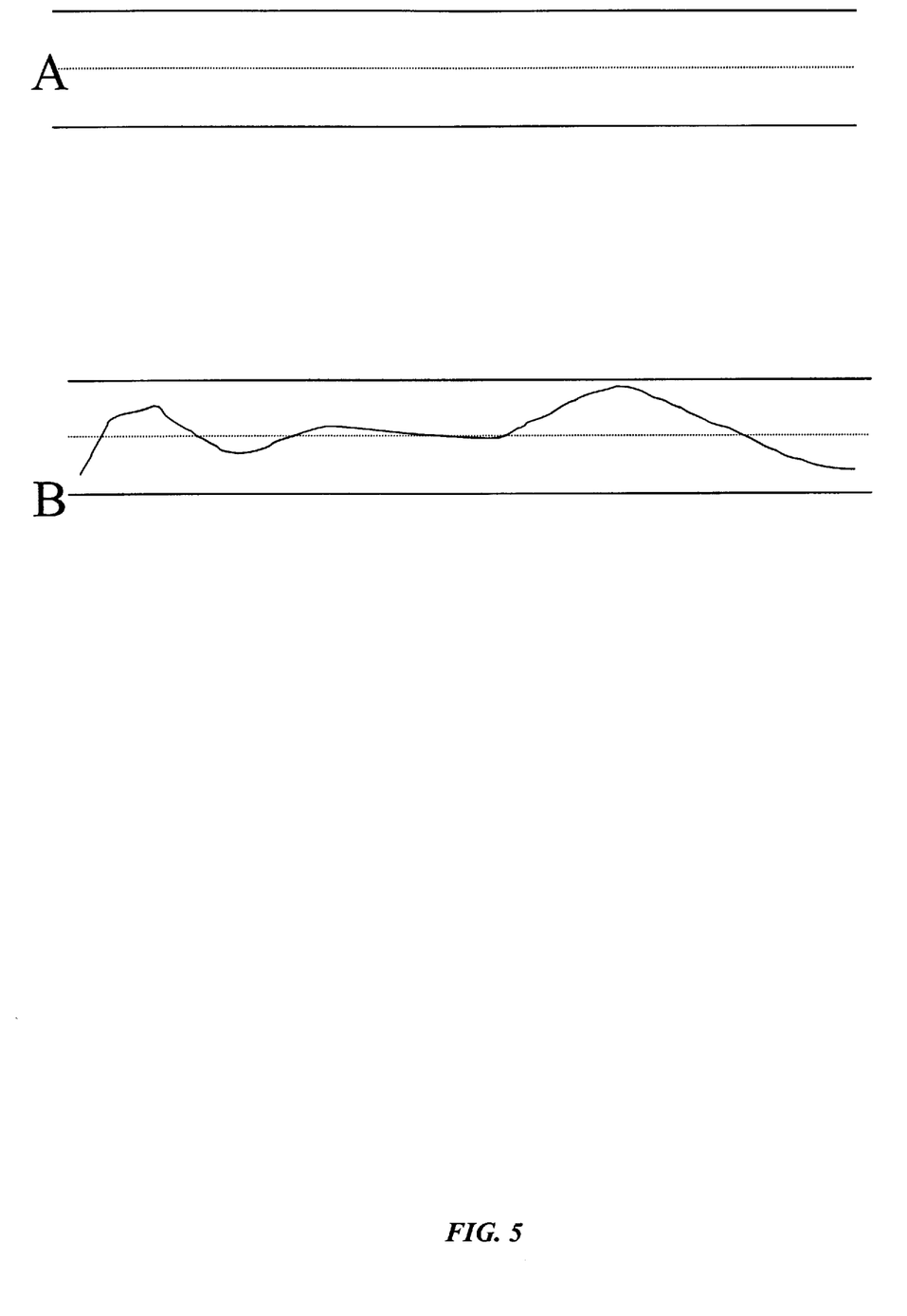
FIG. 5 (A–B) illustrates a process of the present invention. Panel A and B illustrates a process control plot wherein the dotted line represents the acceptably data and the solid lines represent acceptability quotient. Panel B illustrate a process control strip chart of an in-line process.

Moreover, an agricultural product can be measured in-line. The measurement is done in-line with the user specifying acceptability limits. The system generates a typical process control output. This process control output is illustrated in FIG. 5. In this plot, the dotted line represents the acceptably data set and the solid lines represent the limits of the circle defined by the acceptability quotient. As new samples are measured, they are plotted against these control points and a running strip chart of the process, as monitored by smell, is created. From this data, a process can be monitored where the control feature is smell.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for monitoring a quality of an agricultural product, said method comprising:
   i) training an array of sensors with a fluid associated with a known agricultural product to generate a first residual standard deviation $(s(e)^2)$;
   ii) contacting said array of sensors with said fluid associated with an unknown agricultural product to generate a second residual standard deviation $(s(e_m)^2)$;
   iii) calculating a ratio between said second residual standard deviation and said first residual standard deviation $(s(e_m)^2/s(e)^2)$; and
   iv) comparing said ratio with an acceptability quotient $(F_{1,df,\alpha})$, wherein said acceptability quotient is user selected, thereby monitoring said quality of said agricultural product.

2. A method in accordance with claim 1, wherein said sensor array comprises at least one member selected from the group consisting of inorganic metal oxide semiconductor sensors, organic conducting polymer sensors, mass sensitive piezoelectric sensors and nonconducting/conducting, regions sensors.

3. A method in accordance with claim 1, wherein said quality is microorganism detection.

4. A method in accordance with claim 1, wherein said microorganism is a member selected from the group consisting of *E. coli* 0157:H7, salmonella, *Staphylococcus aurus*, and *Listeria monocytogenes*.

5. A method in accordance with claim 1, wherein said array of sensors are on-line.

6. A method in accordance with claim 1, wherein said quality is rancidity.

7. A method in accordance with claim 1, wherein said quality is authenticity.

8. A method in accordance with claim 1, wherein said quality is process monitoring.

9. A method in accordance with claim 1, wherein said quality is fruit ripening.

10. A method in accordance with claim 1, wherein said array of sensors is in a handheld device.

11. A method in accordance with claim 1, wherein said comparison is performed using a pattern recognition algorithm which is a member selected from the group consisting of principal component analysis, Fisher linear discriminant analysis, soft independent modeling of class analogy, K-nearest neighbors, and canonical discriminant analysis.

12. A method for monitoring contamination in an agricultural product, said method comprising:
   (i) training an array of sensors with a fluid associated with a known agricultural product to generate a first residual standard deviation $(s(e)^2)$;
   (ii) contacting said array of sensors with said fluid associated with an unknown agricultural product to generate a second residual standard deviation $(s(e_m)^2)$;
   (iii) calculating a ratio between said second residual standard deviation and said first residual standard deviation $(s(e_m)^2/s(e)^2)$; and
   (iv) comparing said ratio with an acceptability quotient $(F_{1,df,\alpha})$, wherein said acceptability quotient is user selected, thereby monitoring contamination in said agricultural product.

13. A method in accordance with claim 12, wherein said contamination is caused by a pathogenic microorganism.

14. A method in accordance with claim 13, wherein said microorganism is a member selected from the group consisting of a bacterium, a virus, and fungus.

* * * * *